United States Patent
Morré et al.

(10) Patent No.: US 7,192,612 B2
(45) Date of Patent: Mar. 20, 2007

(54) COMPOSITIONS AND METHODS BASED ON SYNERGIES BETWEEN CAPSICUM EXTRACTS AND TEA CATECHINS FOR PREVENTION AND TREATMENT OF CANCER

(75) Inventors: D. James Morré, West Lafayette, IN (US); Dorothy M. Morré, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 46 days.

(21) Appl. No.: 10/886,159

(22) Filed: Jul. 6, 2004

(65) Prior Publication Data

US 2005/0031716 A1 Feb. 10, 2005

Related U.S. Application Data

(63) Continuation-in-part of application No. 10/081,903, filed on Feb. 22, 2002, now Pat. No. 6,759,064.

(60) Provisional application No. 60/530,114, filed on Dec. 17, 2003, provisional application No. 60/270,557, filed on Feb. 22, 2001.

(51) Int. Cl.
*A51K 36/82* (2006.01)
*A61K 36/81* (2006.01)
*A61K 9/22* (2006.01)
*A61K 31/35* (2006.01)
*A61K 31/05* (2006.01)

(52) U.S. Cl. ...................... 424/729; 424/760; 424/468; 514/456; 514/732; 514/738

(58) Field of Classification Search ...................... None
See application file for complete search history.

(56) References Cited

U.S. PATENT DOCUMENTS 4,238,508 A 12/1980 Nelson (Continued)

FOREIGN PATENT DOCUMENTS

EP 0089710 9/1983

(Continued)

OTHER PUBLICATIONS

Ahmad et al. (1998) "Cancer Chemoprevention by Tea Polyphenols," *Nutrition and Chemical Toxicity*, John Wiley and Sons, Sussex, England, pp. 301-343.

(Continued)

*Primary Examiner*—Christopher R. Tate
(74) *Attorney, Agent, or Firm*—Greenlee, Winner and Sullivan, PC (57) ABSTRACT

The invention described herein encompasses methods and compositions of preventing or treating cancer comprising the administration of a combination of therapeutically effective amount of catechins, a group of polyphenols found in green tea, and *Capsicum* extracts. Compositions of catechins include but not limited to, epigallocatechin gallate (EGCg), epicatechin (EC), epicatechin gallate (ECG), epigallocatechin (EGC). The unique compositions of the invention contain various combinations of the catechins and *Capsicum* extracts, in combination with each other or other therapeutic agents and are used to treat primary and metastatic cancers in humans. The invention also encompasses the varying modes of administration of the therapeutic compounds, including a formulation which may be used as a therapeutic compound for the treatment of cancer or as a dietary supplement for the prevention of cancer.

18 Claims, 2 Drawing Sheets

U.S. PATENT DOCUMENTS

| | | | |
|---|---|---|---|
| 4,313,958 | A | 2/1982 | LaHann |
| 4,401,663 | A | 8/1983 | Buckwalter et al. |
| 4,424,205 | A | 1/1984 | LaHann et al. |
| 4,443,473 | A | 4/1984 | Buckwalter et al. |
| 4,460,602 | A | 7/1984 | Buckwalter et al. |
| 4,493,848 | A | 1/1985 | LaHann et al. |
| 4,532,139 | A | 7/1985 | Janusz et al. |
| 4,544,668 | A | 10/1985 | Janusz et al. |
| 4,544,669 | A | 10/1985 | LaHann et al. |
| 4,564,633 | A | 1/1986 | LaHann et al. |
| 5,354,556 | A | 10/1994 | Sparks et al. |
| 5,391,568 | A | 2/1995 | Chung |
| 5,461,075 | A | 10/1995 | Oneill et al. |
| 5,569,673 | A | 10/1996 | Morre et al. |
| 5,605,810 | A | 2/1997 | Morre et al. |
| 5,773,075 | A * | 6/1998 | Todd .......................... 426/638 |
| 5,876,728 | A | 3/1999 | Kass et al. |
| 5,989,557 | A | 11/1999 | Bombardelli et al. |
| 6,022,718 | A | 2/2000 | Iwai et al. |
| 6,063,381 | A | 5/2000 | Staggs |
| 6,096,359 | A | 8/2000 | Bombardelli et al. |
| 6,168,795 | B1 * | 1/2001 | DJang .......................... 424/729 |
| 6,201,014 | B1 | 3/2001 | Gardiner |
| 6,410,052 | B1 | 6/2002 | Morre et al. |
| 6,410,061 | B1 | 6/2002 | Morre et al. |
| 6,428,818 | B1 | 8/2002 | Morre et al. |
| 6,652,890 | B2 | 11/2003 | Morre et al. |
| 6,759,064 | B2 | 7/2004 | Morre et al. |

FOREIGN PATENT DOCUMENTS

| | | |
|---|---|---|
| EP | 282127 | 9/1988 |
| GB | 2168974 | 7/1986 |
| GB | 2168975 | 7/1986 |
| GB | 2168976 | 7/1986 |

OTHER PUBLICATIONS

Ahmad et al. (1999) "Green Tea Polyphenols and Cancer: Biologic Mechanisms and Practical Implications," *Nutr. Rev.* 57:78-83.

Ahmad et al. (Dec. 1997) "Green tea constituent epigallocatechin-3-gallate and induction of apoptosis and cell cycle arrest in human carcinoma cells," *J. Nat. Cancer Inst.* 89:1881-1886.

Brightman et al. (1992) "A Growth Factor- and Hormone-Stimulated NADH Oxidase from Rat Liver Plasma Membrane," *Biochim. Biophys. Acta.* 1105:109-117.

Brown et al. (1969) "Butyramide-utilizing Mutants of *Pseudomonas aeruginosa* 8602 which Produce an Amidase with Altered Substrate Specificity," *J. Gen. Microbiol.* 57(2):273-285.

Bruno et al. (1992) "Stimulation of NADH Oxidase Activity from Rat Liver Plasma Membranes by Growth Factors and Hormones is Decreased or Absent with Hepatoma Plasma Membranes," *Biochem J.* 284:625-628.

Caterina et al. (2001) "The Vanilloid Receptor: A Molecular Gateway to the Pain Pathway," *Annu. Rev. Neurosci.* 24:487-517.

Chan et al. (1997) "Inhibition of Inducible Nitric Oxide Synthase Gene Expresion and Enzyme Activity by Epigallocatechin Gallate, A Natural Product from Green Tea," *Biochem. Pharmacol.* 54:1281-1286.

Chen et al. (1998) "Green Tea Epigallocatechin Gallate Shows a Pronounced Grpwth Inhibitory Effect on Cancerous Cells but not on Their Normal Counterparts," *Cancer Lett.* 129:173-179.

Chen et al. (1996) "Tamoxifen Induces TGF-β-1 Activity and Apoptosis of Human MCF-7 Breast Cancer Cells in Vitro," *J. Cell. Biochem.* 61:9-17.

Chueh et al. (1997) "A 33.5-kDa Heat- and Protease-Resistant NADH Oxidase Inhibited by Capsaicin from Sera of Cancer Patients," *Arch. Biochem. Biophys.* 342:38-44.

Chueh et al. (1997) "The Hormone-responsive NADH Oxidase of the Plant Plasma Membrane Has Properties of a NADH: Protein Disulfide Reductase," *J. Biol. Chem.* 272:11221.

DeHann et al. (1997) "NADH Oxidase Activity Present on Both the External and Internal Surfaces of Soybean Plasma Membranes," *Biochim. Biophys. Acta.* 1328:99-108.

Dong et al. (Oct. 1997) "Inhibition of Tumor Promoter-induced Activator Protein 1 Activation and Cell Transformation by Tea Polyphenols, (-)-Epigallocatechin Gallate, and Theaflavins," *Cancer Res.* 57:4414-4419.

Fujiki et al. (1998) "Cancer Inhibition by Green Tea," *Mutat. Res.* 402:307-310.

Holzer et al. (1979) "Nociceptive Threshold After Neonatal Capsaicin Treatment," *Eur. J. Pharm.* 58:511-514.

Jancso et al. (1980) "Effect of Capsaicin on Morphine Analgesia Possible Involvement of Hypothalamic Structures," *Naunyn-Schmiedeberg's Arch. Pharmacol.* 311:285-288.

Khan et al. (1988) "Inhibition of the Skin Tumorigenicity of (±)-7β, 8α-Dihydroxy-9, 10α-Epoxy-7,8,9,10-Tetrahydrobenzo[a]pyrene by Tannic Acid, Green Tea Polyphenols and Quercetin in Sencar Mice," *Cancer Lett.* 42:7-12.

Kishi et al. (1999)"The Plasma Membrane NADH Oxidase of HeLa Cells has Hydroquinone Oxidase Activity," *Biochem. Biophys. Acta.* 1412:66-77.

Liang et al. (1997) "Suppression of Extracellular Signals and Cell Proliferation Through EGF Receptor Binding by(-)-Epigallocation Gallate in Human A431 Epidermoid Carcinoma Cells," *J. Cell. Biochem.* 67:55-65.

Liao et a. (1995) "Growth Inhibition and Regression of Human Prostate and Breast Tumors in Athymic Mice by Tea Epigallocatechin Gallate," *Cancer Lett.* 96:239-243.

Lin et al. (Sep. 1997) "(—)-Epigallocatechin-3-gallate Blocks the Induction of Nitric Oxide Synthase by Down-Regulating Lipopolysaccharide-Induced Activity of Transcription Factor Nuclear Factor-κB," *Mol. Pharmacol.* 52:465-472.

Morré (1994) "Hormone- and Growth Factor-Stimulated NADH Oxidase," *J. Bioenerg. Biomemb.* 26:421-433.

Morré (1998)"A Multifunction Ectoprotein of the Eukaryotic Cell Surface," in *Plasma Membrane Redox Systems and their Role in Biological Stress and Disease,* Kluwer Academic Publishers, Dordrecht, The Netherlands, pp. 121-156.

Morré et al. (1995) "Mechanism of Killing of HeLa Cells by the Antitumor Sulfonylurea, N-(4-methylphenylsulfonyl)-N'-(4-chlorophenyl)urea (LY181984)," *Protoplasma* 184:188-195.

Morré et al. (Mar. 1995) "Capsaicin Inhibits Preferentially the NADH Oxidase and Growth of Transformed Cells in Culture," *Proc. Natl. Acad. Sci. U.S.A.* 92:1831-1835.

Morré et al. (1995) "The Antitumor Sulfonylurea N-(4methylphenylsulfonyl)-N'-(4-chlorophenyl) urea (LY181984) Inhibits NADH Oxidase Activity of HeLa Plasma Membranes," *Biochim. Biophys. Acta.* 1240:11-17.

Morré et al. (1996) "Capsaicin Inhibits Plasma Membrane NADH Oxidase and Growth of Human and Mouse Melanoma Lines," *Eur. J. Can.* 32A:1995-2003.

Morré et al. (1997) "Is the Drug-Responsive NADH Oxidase of the Cancer Cell Plasma Membrane a Molecular Target for Adriamycin," *J. Biomemb. Bioeng.* 29:269-280.

Morré et al. (1991) "NADH Oxidase of Plasma Membranes," *J. Bioenerg. Biomemb.* 23:469-489.

Komori et al. (1993) "Anticarcinogenic Activity of Green Tea Polyphenols," *Jpn. J. Clin. Oncol.* 23:186-190.

Paschka et al. (1998) "Induction of Apoptosis in Prostate Cancer Cell Lines by the Green Tea Component, (-)-Epigallocatechin-3-Gallate," *Cancer Lett.* 130:1-7.

Piazza et al. (Jul. 1995) "Antineoplastic Drugs Sulindac Sulfide and Sulfone Inhibit Cell Growth by Inducing Apoptosis," *Cancer Res.* 55:3110-3116.

Sadzuka et al. (Jan. 1998) "Modulation of Cancer Chemotherapy by Green Tea," *Clin. Cancer Res.* 4:153-156.

Stoner et al. (1995) "Polyphenols as Cancer Chemopreventive Agents," *J. Cell. Biochem.* 22:169-180.

Suganuma et al. (Jan. 1999) "Synergistic Effects of (-)-Epigallocatechin Gallate with (-)-Epicatechin, Sulindac, or Tamoxifen on Cancer-preventive Activity in the Human Lung CancerCell Line PD-9,"*Can. Res.* 59:44-47.

Sugiyama et al (1998) "Enhancing Effects of Green Tea Components on the Antitumor Activity of Adriamycin Against M5076 Ovarian Sarcoma," *Can. Lett.* 133:19-26.

Sugunama et al. (Oct. 1998) "Wide Distribution of [3H](-)-Epigallocatechin Gallate, a Cancer Preventive Tea Polyphenol, in Mouse Tissue," *Carcinogenesis* 19:1771-1776.

Sugunama et al. (Aug. 1996) "A New Process of Cancer Prevention Mediated Through Inhibition of Tumor Necrosis Factor Alpha Expression," Can. Res. 56:3711-3715.

Sun et al. (Nov. 1987) "NADH Diferric Transferrin Reductase in Liver Plasma Membrane," *J. Biol. Chem.* 262:15915-15921.

Wang et al. (Feb. 1989) "Protection Against Polycyclic Aromatic Hydrocarbon-Induced Skin Tumor Initiation in Mice by Green Tea Polyphenols," *Carcinogenesis* 10:411-415.

Wang et al. (1994) "Inhibitory Effects of Black Tea, Green Tea, Decaffeinated Black Tea, and Decaffeinated Green Tea on Ultraviolet B Light-induced Skin Carcinogenesis in 1,12-Dimethylbenz[a]anthracene-initiated SKH-1 Mice," *Cancer Res.* 54:3428-3435.

Weisburger (1997) "Tea and Health: A Historical Prospective," *Cancer Lett.* 114:315-317.

Wright et al. (Jun. 1994) "Inhibition of Apoptosis as a Mechanism of Tumor Promotion," *FASEB J.* 8:654-660.

Yaksh et al. (1979) "Intrathecal Capsaicin Depletes Substance P in Rat Spinal Cord and Produces Prolonged Thermal Analgesia," *Science* 206:481-483.

Yang et al. (Apr. 1998) "Inhibition of Growth and Induction of Apoptosis in Human Cancer Cell Lines by Tea Polyphenols," *Carcinogenesis* 19:611-616.

http://www.capsibiol-t.com Capsibiol-T: Green Tea and Capsicum Anticancer Supplement.

http://www.newcancerresearch.com New Cancer Research—Capsibiol-T® Targets and Inhibits the tNOX Protein of Cancer Cells.

* cited by examiner

COMPOSITIONS AND METHODS BASED ON SYNERGIES BETWEEN CAPSICUM EXTRACTS AND TEA CATECHINS FOR PREVENTION AND TREATMENT OF CANCER

CROSS-REFERENCE TO RELATED APPLICATIONS

This application claims the benefit of U.S. Provisional Application 60/530,114 filed Dec. 17, 2003, and this application is a continuation-in-part of U.S. application Ser. No. 10/081,903, filed Feb. 22, 2002, now U.S. Pat. No. 6,759,064 which application claims benefit of U.S. Provisional Application 60/270,557, filed Feb. 22, 2001.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

BACKGROUND OF THE INVENTION

The present invention relates to novel methods and compositions which utilize catechins, including but not limited to, epigallocatechin gallate (EGCg), epicatechin (EC), epicatechin gallate (ECG), and epigallocatechin (EGC), which are found in varying levels in tea leaves, in combination with *Capsicum* extracts. The compositions of the invention contain various amounts of the catechins, including combinations of catechins and *Capsicum* extracts, or catechins, *Capsicum* extracts, and other therapeutic agents. The invention also encompasses the varying modes of administration of the compositions of the subject invention as a therapeutic compound for the treatment of cancer or as a dietary supplement for the prevention of cancer.

Tea is generally in the form of black, oolong, and green tea, all originating from the tea plant, *Camellia sinensis*. Tea is cultivated in approximately thirty countries worldwide, and is consumed globally. Although the level of tea consumption varies around the world, it is believed that tea consumption is second only to water (Ahmad et al., 1998, Nutrition and Chemical Toxicity, John Wiley and Sons, Sussex, England, pp. 301–343). Black tea is consumed predominantly in Western and some Asian countries and green tea is consumed predominantly in China, Japan, India, and a few countries in North Africa and the Middle East (Ahmad et al., 1998, Nutrition and Chemical Toxicity, John Wiley and Sons, Sussex, England, pp. 301–343).

Green tea has been prized as a traditional tonic and has been widely consumed in East Asia. Recent studies have attempted to link green tea to antioxidant benefits including protection against the damage caused by cigarette smoke, pollution, stress, and other toxins (for an overview, see e.g., Mitscher, 1998, The Green Tea Book, Avery Publishing Group, Garden City Park, N.Y. and Weisburger, 1997, Can. Lett. 114:315–317).

An empirical link between green tea and its cancer prevention properties was made in the late 1980s (Khan et al., 1988, Can. Lett. 42:7–12 and Wang et al., 1989, Carcinogenesis 10:411–415). Epidemiological studies show that cancer onset of patients in Japan who had consumed ten cups of green tea per day was 8.7 years later among females and 3 years later among males, compared with patients who had consumed under three cups per day (Fujiki et al., 1998, Mutation Res. 402:307–310). As such, a possible relationship between high consumption of green tea and low incidence of prostate and breast cancer in Asian countries where green tea consumption is high has been postulated (Liao et al., 1995, Can. Lett. 96:239–243 and Stoner and Mukhtar, 1995, J. Cell. Biochem. 22:169–180). However, because of the many variables in lifestyle inherent to such a study, a definitive link between green tea and its cancer prevention effects could not be concluded.

Scientists have now identified many of the natural substances in green tea that may provide the majority of its health benefits. One class of chemicals that has attracted much study is the polyphenols, also known as catechins.

The polyphenols describe a class of substituted phenolic compounds that are known as flavanols or catechins. The polyphenols in green tea that have been identified are catechin (C), epicatechin (EC), gallocatechin (GC), gallocatechin gallate (GCG), epigallocatechin (EGC), epicatechin gallate (ECG), and epigallocatechin gallate (EGCg). In addition, caffeine, theobromine, theophylline, and phenolic acids, such as gallic acid, are also present as constituents of green tea in smaller quantities than the polyphenols (Ahmad et al., 1998, Nutrition and Chemical Toxicity, John Wiley and Sons, Sussex, England, pp. 301–343).

Epigallocatechin gallate (EGCg), the major catechin in green tea, has been the focus of many studies to determine if it is responsible for the antioxidant and anti-carcinogenic effects of green tea, as reviewed by Ahmad and Mukhtar, 1999, Nutr. Rev. 57:78–83. The administration of a pharmacologically effective amount of EGCg has been alleged to reduce the incidence of lung cancer in a mammal (U.S. Pat. No. 5,391,568). A bioavailability study showed that frequent green tea consumption results in high levels of EGCg in various body organs, suggesting that green tea consumption may protect against cancers localized to different sites of the body (Sugunama et al., 1998, Carcinogenesis 19:1771–1776).

EGCg has been implicated in blocking DNA transcription of a number of genes in cancer cell lines. For example, in the human epidermal carcinoma cell line A43 1, EGCg inhibits the DNA and protein synthesis of the growth factor receptors epidermal growth factor receptor (EGF-R), platelet-derived growth factor receptor (PDGF-R), and fibroblast growth factor receptor (FGF-R) (Liang et al., 1997, J. Cell. Biochem. 67:55–65). EGCg has also been implicated in blocking transcription of nitric oxide (NO) synthase by inhibiting the binding of transcription factor NFhB to the NO synthase promotor (Lin and Lin, 1997, Mol. Pharmacol. 52:465–472 and Chan et al., 1997, Biochem. Pharmacol. 54:1281–1286). In the tumor cell line JB6, EGCg inhibits AP-1 transcriptional activity (Dong et al., 1997, Can. Res. 57:4414–4419). These results suggest that EGCg may prevent cancer at the level of gene transcription, i.e., by blocking the DNA synthesis of genes involved in signal transduction pathways.

Further, the focus of many other studies has been the effect of EGCg on apoptosis, or programmed cell death. Apoptosis differs from necrosis, and is regarded as an ideal mechanism for the elimination of cells. Studies have shown that several anti-cancer preventative agents may induce apoptosis, and conversely, several tumor-promoting agents inhibit apoptosis (Wright et al., 1994, FASEB J 8:654–660 and Ahmad and Mukhtar, 1999, Nutr. Rev. 57:78–83).

Much of the prior work in the art has attempted to determine what, if any, effect EGCg has on the growth inhibition and apoptosis induction of cancer cells. A differential growth inhibitory effect was reported in human colorectal cancer cells CaCo-2, breast cancer cells Hs578T, and their non-cancer cell counterparts (Ahmad and Mukhtar, 1999, Nutr. Rev. 57:78–83). EGCg has been implicated in the growth arrest and subsequent induction of apoptosis following cell growth inhibition has been shown in virally transformed fibroblast cells WI 138, human epidermal carcinoma cells A431, lung cancer tumor cells H61 1, prostate cancer cell lines LNCaP, PC-3, and DU145, human carcinoma keratinocytes HaCaT, and mouse lymphoma cells LY-R (Chen et al., 1998, Can. Lett. 129:173–179; Ahmad et al., 1997, J. of the Nat. Can. Inst. 89:1881–1886; Yang et al., 1998, Carcinogenesis 19:611–616; Paschka et al., 1998, Can. Lett. 130:1–7; and Ahmad and Mukhtar, 1999, Nutr. Rev. 57:78–83). In studies where the apoptotic response was studied in cancer cells versus their non-cancer counterparts, e.g., human carcinoma keratinocytes HaCaT versus normal human epidermal keratinocytes, the apoptotic response to EGCg was reported to be specific to the cancer cells (Ahmad et al., 1997, J. Nat. Can. Inst. 89:1881–1886).

It has been suggested that EGCg-induced apoptosis may result from either cell cycle arrest and/or $H_2O_2$ production (Ahmad et al., 1997, J. Nat. Can. Inst. 89:1881–1886; Fujiki et al., 1998, Mutat. Res. 402:307–310; and Yang et al., 1998, Carcinogenesis 19:611–616). EGCg may be involved in the growth regulation of human epidermal carcinoma cells A431 by causing cell cycle arrest of the Go to G, phase (Ahmad et al., 1997, J. Nat. Can. Inst. 89:1881–1886). EGCg has also been implicated in phase arrest between G2 to M phase of the cell cycle in human lung cancer cells (Fujiki et al., 1998, Mutat. Res. 402:307–310). In the EGCg induced inhibition of human lung cancer cells, it was suggested that the tumor necrosis factor (TNF) a pathway that is the mode of action of EGCg. Alternatively, the EGCg-induced apoptosis of the lung cancer tumor cells H611 is inhibited by catalase, suggesting the $H_2O_2$ production as a probable cause of apoptosis (Yang et al., 1998, Carcinogenesis 19:611–616).

Despite the above studies, the efficacy of EGCg as a single agent therapy for the prevention of cancer is still unclear. Moreover, the efficacy of EGCg as a therapeutic drug to treat or reverse cancer in a patient is unknown. Although the focus of much of the prior research has been on EGCg, the putative biological functions of some of the other catechins has been examined. For example, both epicatechin gallate (ECG) and epigallocatechin (EGC) have been reported to be as effective as EGCg in inducing apoptosis of human epidermal carcinoma cells A431 at similar concentrations, whereas epicatechin (EC) did not show a similar effect (Ahmad et al., 1997, J. of the Nat. Can. Inst. 89:1881–1886). Growth inhibition in lung tumor cell lines H661 and H1299 was also observed with EGCg and EGC, whereas ECG and EC were less effective (Yang et al., 1998, Carcinogenesis 19:611–616).

Catechins have been implicated in growth inhibition of the human lung cancer cell line PC-9, with the order of catechin potency being reported as EGCg=ECG>EGC EC (Okabe et al., 1993, Jpn. J. Clin. Oncol. 23:186–190). It has also been demonstrated that catechin combinations of EGCg and EC, ECG and EC, and EGC and EC induce apoptosis of the human lung cancer cell line PC-9 in vitro (Suganuma et al., 1999, Can. Res. 59:44–47). EC is thought to enhance incorporation of EGCg into the cells, which is thought to inhibit TNF a release resulting in the induction of apoptosis (Suganuma et al., 1999, Can. Res. 59:44–47).

Green tea extract, an important source of EGCg, has previously been reported to enhance the effect of the anticancer agents, e.g., adriamycin and doxorubicin (Sugiyama and Sadzuka, 1998, Can. Lett. 133:19–26 and Sadzuka et al., 1998, Clin. Can. Res. 4:153–156). Green tea in combination with adriamycin inhibits tumor growth in M5076 ovarian sarcoma cells, whereas adriamycin alone does not inhibit tumor growth in M5076 ovarian sarcoma cells (Sugiyama and Sadzuka, 1998, Can. Lett. 133:19–26). A similar effect is observed with green tea extract and doxorubicin on the same M5076 ovarian sarcoma cell line. Green tea extract, in combination with doxorubicin, also enhances the inhibitory growth effect on Ehrlich ascites carcinoma tumors in tumor-bearing mice, presumably by increasing the concentration of doxorubicin concentration in the tumor, but not in normal tissue (Sadzuka et al., 1998, Clin. Can. Res. 4:153–156).

EGCg has also been shown to enhance the effect of cancer prevention drugs in vitro. For example, EGCg has been shown to enhance the apoptotic effect of sulindac and tamoxifin, presumably by EGCg enhancing the intracellular concentration of the cancer prevention drugs. (Suganuma et al., 1999, Can. Res. 59:44–47). Both sulindac and tamoxifin induce apoptosis of human cancer cells and inhibit TNF a release from BALB/c-3T3 cells (Piazza et al., 1995, Can. Res. 55:3110–3116; Chen et al., 1996, J. Cell. Biochem. 61:9–17; and Sugunama et al., 1996, Can. Res. 56:3711–3715).

U.S. Pat. Nos. 6,428,818; 6,410,052; 6,652,890; 6,410,061 and 6,759,064 discuss tea-derived catechins and compositions for treating and/or preventing cancer in a mammal. U.S. Pat. No. 6,759,064 also discusses synergistic activities of catechins and vanilloids (e.g., capsaicin) in anticancer strategies. Each of these patents is incorporated by reference in its entirety.

The active ingredients of extracts of the fruit (peppers) of the *Capsicum* species, with high amounts being found in the well known chili pepper, are believed to be the capsaicinoids. The capsaicinoids represent a group of natural products that are vanillylamides of monocarboxylic acids of varying chain lengths from C-8 to C-11 and of varying degrees of unsaturation.

Capsaicin is the most widely studied capsaicinoid. According to World Health Organization statistics, in countries where diets are traditionally high in capsaicin, the cancer death rates for men and women are significantly lower than they are in countries with less chili pepper consumption.

A unique plasma membrane NADH oxidase (NOX), a unique cell surface protein with hydroquinone (NADH) oxidase and protein disulfide-thiol interchange activities that is responsive to hormone and growth factors has been identified (Brightman et al., 1992, Biochim. Biophys. Acta 1105:109–117; Morre, 1994, J. Bioenerg. Biomemb. 26:421–433; and Morre, 1998, Plasma Membrane Redox Systems and their Role in Biological Stress and Disease, Klewer Academic Publishers, Dordrecht, The Netherlands, pp. 121–156). Further, a hormone-insensitive and drug-responsive form of NOX designated tNOX which is specific to cancer cells has been reported (Bruno et al., 1992, Biochem. J. 284:625–628; Morre and Morre, 1995, Protoplasma 184:188–195; Morre et al., 1995, Proc. Natl. Acad. Sci. U.S.A. 92;1831–1835; Morre et al., 1995, Biochim. Biophys. Acta 1240:11–17; Morre et al., 1996, Eur. J. Can. 32A:1995–2003; and Morre et al., 1997, J. Biomemb. Bioenerg. 29:269–280).

Because the NOX protein is located at the external plasma membrane surface and is not transmembrane, a functional role as an NADH oxidase is not considered likely (Morre, 1994, J. Bioenerg. Biomemb. 26:421–433; DeHahn et al., 1997, Biochim. Biophys. Acta 1328:99–108; and Morre, 1998, Plasma Membrane Redox Systems and Their Role in Biological Stress and Disease, Klewer Academic Publishers, Dordrecht, The Netherlands, pp. 121–156). While the oxidation of NADH provides a basis for a convenient method to assay the activity, the ultimate electron physiological donor is most probably hydroquinones with specific activities for hydroquinone oxidation greater than or equal to that of NADH oxidation and/or protein thiol-disulfide interchange (Kishi et al., 1999, Biochim. Biophys. Acta 1412: 66–77).

CNOX was originally defined as a drug-indifferent constitutive NADH oxidase activity associated with the plasma membrane of non-transformed cells that was the normal counterpart to tNOX (Morre, 1998, Plasma Membrane Redox Systems and Their Role in Biological Stress and Disease, Kiewer Academic Publishers, Dordrecht, The Netherlands, pp. 121–156). Indeed, a 36 kD protein isolated from rat liver and from plants has NOX activity that is unresponsive to tNOX inhibitors (Brightman et al., 1992, Biochim. Biophys. Acta 1105: 109–117).

While cancer cells exhibit both drug-responsive and hormone and growth factor-indifferent (tNOX) as well as drug inhibited and hormone and growth factor dependent (CNOX) activities, non-transformed cells exhibit only the drug indifferent hormone- and drug-responsive CNOX. Among the first descriptions of so-called constitutive or CNOX activity of non-transformed cells and tissues was where the activity of rat liver plasma membranes was stimulated by the growth factor, diferric transferrin (Sun et al., 1987, J. Biol. Chem. 262:15915–15921). Subsequent work demonstrated that the observed NADH oxidation was catalyzed by a unique enzyme exhibiting responsiveness to several hormones and growth factors (Bruno et al., 1992, Biochem J. 284:625–628). Unlike mitochondrial oxidases, the hormone-stimulated NADH oxidase activity of rat liver plasma membranes is not inhibited by cyanide (Morre, 1994, J. Bioenerg. Biomemb. 26: 421–433). The enzyme also was distinguished from other oxidase activities by its response to several common oxidoreductase inhibitors, e.g., catalase, azide and chloroquine, as well as to various detergents e.g., sodium cholate, Triton X-100 and CHAPS (Morre and Brightman, 1991, J. Bioenerg. Biomemb. 23:469–489 and Morre et al., 1997, J. Biomemb. Bioenerg. 29:269–280). Like tNOX of cancer cells, CNOX is a unique membrane-associated protein that is capable of oxidizing NADH but has an activity which is modulated by hormones and growth factors.

Cancer is characterized primarily by an increase in the number of abnormal cells derived from a given normal tissue, invasion of adjacent tissues by these abnormal cells, and lymphatic or blood-borne spread of malignant cells to regional lymph nodes and to distant sites (metastasis). Clinical data and molecular biologic studies indicate that cancer is a multistep process that begins with minor pre-neoplastic changes, which may under certain conditions progress to neoplasia.

Pre-malignant abnormal cell growth is exemplified by hyperplasia, metaplasia, or most particularly, dysplasia (for review of such abnormal growth conditions, see Robbins and Angell, 1976, Basic Pathology, 2d Ed., W. B. Saunders Co., Philadelphia, pp. 68–79) Hyperplasia is a form of controlled cell proliferation involving an increase in cell number in a tissue or organ, but without significant alteration in structure or function.

As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium.

Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

The neoplastic lesion may evolve clonally and develop an increasing capacity for invasion, growth, metastasis, and heterogeneity, especially under conditions in which the neoplastic cells escape the host's immune surveillance (Roitt, Brostoff, and Kale, 1993, *Immunology*, 3rd ed., Mosby, St. Louis, pp. 17.1–17.12).

There remains a need for treatment of cancer that does not have the adverse effects generally caused by non-selectivity, of conventional chemotherapeutic agents. None of the above studies, which are not to be construed as an admission that any of the above studies is prior art have evaluated the efficacy of catechins in combination with *Capsicum* extracts for the treatment of cancer. In contrast, the present inventors have identified a cancer-specific isoform of a unique plasma membrane NADH oxidase (tNOX) which is inhibited by the catechins and *Capsicum* extracts (optionally treated with amidase, with bacteria or fungi, or extracts from bacterial or fungal cells or their cultures). Furthermore, the studies cited supra have hypothesized that EGCg mediates its effects intracellularly, since EGCg incorporation into the cell seems to be a prerequisite for the inhibition of TNF α release. Inhibition of tNOX, an extracellular membrane-associated protein) by EGCg, and synergistically with other catechins, *Capsicum* extracts, and anti-cancer agents, results in the selective inhibition of cancer cell growth and ultimately, apoptosis.

BRIEF SUMMARY OF THE INVENTION

The invention encompasses formulations comprising catechins and *Capsicum* extracts, which are used as therapeutic compounds for the prevention and treatment of cancer or as a dietary supplement that offers white blood cell protection and maintains healthy blood. Specific therapeutic regimens, pharmaceutical compositions, and kits are also provided by the invention.

In one embodiment, the invention described herein comprises the administration of catechins in combination with *Capsicum* extracts, to a mammal as a dietary supplement for the prevention of cancer. In a preferred embodiment, the mammal is a human.

In one embodiment, the invention described herein comprises the administration of a therapeutically effective amount of catechins in combination with *Capsicum* extracts, to a mammal in need of such therapy. In a preferred embodiment, the mammal is a human. In another embodiment, the invention further encompasses the use of combination therapy to treat cancer.

In a specific embodiment, the catechins comprise a combination of epigallocatechin gallate (EGCg), epicatechin gallate (ECG), epigallocatechin (EGC), and epicatechin (EC) or a combination thereof, with a *Capsicum* extract.

The disclosure is based, in part, on the discovery that epigallocatechin gallate (EGCg), alone and in combination with other catechins, *Capsicum* extracts, and optionally, other anti-cancer therapeutic agents, inhibits the activity of a cancer-specific protein, an isoform of NADH oxidase specific to cancer cells (tNOX). The inhibition of tNOX results in the inhibition of cell growth, and ultimately, apoptosis of the cancer cell, whereas normal cells (which lack tNOX but instead express the isoform CNOX) are less affected. Thus, the invention provides a potent therapeutic effect without or while reducing the adverse effects on normal, healthy cells.

The effect of the catechins such as EGCg may be reversible, i.e., if the EGCg is removed, cancer cells resume normal rates of growth. Thus, one embodiment of the invention is directed to the administration of a sustained release formulation of catechins provided at least once daily in combination with the catechins and/or *Capsicum* extracts which is provided several times (preferably three times) a day, so that a constant level of the catechins is maintained.

DETAILED DESCRIPTION OF THE INVENTION

As used herein, the term "cancer" describes a diseased state in which a carcinogenic agent or agents causes the transformation of a normal cell into an abnormal cell, the invasion of adjacent tissues by these abnormal cells, and lymphatic or blood-borne spread of malignant cells to regional lymph nodes and to distant sites, i.e., metastasis.

As used herein, the terms "preventing cancer" and "prevention of cancer" mean to inhibit the transformation of a normal cell into an abnormal cell by a carcinogenic agent or agents and/or to inhibit the accumulation of cells expressing cancer-specific genes (e.g., tNOX) to a number which creates clinical symptoms associated with cancer.

As used herein, the terms "treating cancer" and "treatment of cancer" mean to inhibit the replication of cancer cells, to inhibit the spread of cancer, to decrease tumor size, to lessen or reduce the number of cancerous cells in the body, and to ameliorate or alleviate the symptoms of the disease caused by the cancer. The treatment is considered therapeutic if there is a decrease in mortality and/or morbidity.

The term "synergistic" as used herein refers to a combination which is more effective than the additive effects of any two or more single agents. A determination of a synergistic interaction between catechins, *Capsicum* extracts, and optionally, one or more other therapeutic agent may be based on the results obtained from the NOX assays described herein. The results of these assays are analyzed using Chou and Talalay's combination method and Dose-Effect Analysis with Microcomputers' software in order to obtain a Combination Index (Chou and Talalay, 1984, Adv. Enzyme Regul. 22:27–55 and Chou and Chou, 1987, software and manual, Elsevier Biosoft, Cambridge, UK, pp. 19–64).

Combination Index values<1 indicates synergy, values>1 indicate antagonism and values equal to 1 indicate additive effects.

The term "pharmaceutically acceptable carrier" refers to a carrier medium that does not interfere with the effectiveness of the biological activity of the active ingredient, is chemically inert and is not toxic to the patient to whom it is administered.

The term "pharmaceutically acceptable salts" refers to salts prepared from pharmaceutically acceptable non-toxic acids and bases, including inorganic and organic acids and bases.

As used herein the term "pharmaceutically acceptable derivative" refers to any homolog, analog, or fragment corresponding to the catechin formulations as described herein which exhibits anti-cancer activity and is relatively non-toxic to the subject.

The term "therapeutic agent" refers to any molecule, compound or treatment that assists in the treatment of a cancer or the diseases caused thereby.

As used herein, the term "sustained release formulation" refers to any composition that provides slow, controlled, and/or timed release of one or more active ingredients.

As used herein, the term "*Capsicum* extracts" refers to compositions comprising compounds which are effective preventing or delaying the onset of cancer and/or for treating cancer. The extracts can be the dried fruits (including seeds) of *Capsicum* fruits, preferably ground, an aqueous or alcoholic extract of dried *Capsicum* fruits (desirably ground), or an aqueous extract which has been treated with bacterial or fungal enzymes, especially amidase. Amidase treatment is especially desirably in preparations from peppers comprising capsaicin.

The catechins and target proteins defined herein are abbreviated as follows: (t)—catechin, C(-); —epicatechin, EC; gallocatechin, GC; gallocatechin gallate GCG; (-)—epigallocatchin, EGC (-); —epicatechin gallate, ECG (-); —epigallocatechin gallate, EGCg; nicotinamide adenine dinucleotide, NADH; cell surface hydroquinone NADH) oxidase with protein disulfide—thiol isomerase activity, NOX; NOX present in both non-cancer and cancer cells, CNOX; NOX specific to cancer cells, tNOX.

The extraction of active compounds, such as the capsaicinoids, from *Capsicum*, especially *Capsicum frutescens* or certain *Capsicum annuum*, can be accomplished by the use of bacterial enzymes or with aqueous or alcohol extraction of ground dried peppers. Without wishing to bound by any particular theory, it is believed that amidase treatment is useful, at least in part, for reducing the "hot" sensation where the extract is from a so-called "hot pepper", generally characterized with a relatively high concentration of capsaicin. An example of a useful amidase is an amidase isolated from *Pseudomonas aeruginosa*, which is available from Sigma and disclosed by Brown et al., which is incorporated by reference in its entirety (Brown et al., 1969, J. Gen. Microbiol. 1969 57(2):273–85). Desirably the *Capsicum* extract is prepared from the entire dried mature pepper fruit, including the seeds. Ground dried pepper can be used, but where amidase treatment is necessary or desirable, an aqueous or alcoholic extract is prepared prior to the amidase treatment. The particular *Capsicum* fruit is one which is not characterized as a "sweet pepper"; there should be a relatively low sugar content for use in the compositions and methods of the present invention. Extracts of red, green, orange and yellow bell peppers, and pimentos are not suitable for use in the present invention. It is preferred to use *Capsicum* cultivars which have a thin pericarp or fruit wall such that the fruits dry quickly. However, the capsaicin content is not correlated with the effectiveness in the compositions and methods of the present invention is the pericarp, which includes the fruit wall, placenta, and dissepiment (crosswall). Useful types of *Capsicum* fruits include, but are not limited to, those from African bird, Scotch bonnet, habanero, ancho chili, cayenne, poblano, serrano, jalapeno, among others.

The invention encompasses formulations comprising catechins and *Capsicum* extracts, which are used as therapeutic compounds for the prevention and treatment of cancer or as a dietary supplement that offers white blood cell protection and maintains healthy blood levels. Specific therapeutic regimens, pharmaceutical compositions, and kits are also provided by the invention.

In one embodiment, the invention described herein comprises the administration of catechins in combination with *Capsicum* extracts, to a mammal as a dietary supplement for the prevention of cancer. In a preferred embodiment, the mammal is a human.

In another embodiment, the invention described herein comprises the administration of a therapeutically effective amount of catechins, in combination with *Capsicum* extracts, to a mammal in need of such therapy. In a preferred embodiment, the mammal is a human. In another embodiment, the invention further encompasses the use of combination (catechins plus *Capsicum* extracts) therapy to treat cancer.

In a specific embodiment, the catechins comprise a sustained release formulation of epigallocatechin gallate (EGCg), epicatechin gallate (ECG), epigallocatechin (EGC), and epicatechin (EC), in combination with *Capsicum* extracts.

The invention as described throughout is directed to administering the *Capsicum* extract to a subject in either a single formulation containing both the tea catechins together with the *Capsicum* extract in a single formulation or, alternatively, as the tea catechin and *Capsicum* extracts are administered separately. Further, the invention encompasses administering the tea catechins and *Capsicum* extracts substantially simultaneously or alternatively at varying intervals as appropriate for the subject so long as the total effective daily dose is obtained.

The methods of the present invention are based on the discovery that catechins and *Capsicum* extracts inhibit the activity of a cancer-specific protein, an isoform of NADH oxidase specific to cancer cells (tNOX). The inhibition of tNOX results in the inhibition of cell growth, and ultimately, apoptosis of the cancer cell, whereas normal cells (which lack tNOX but instead express the isoform CNOX) are less affected. Thus, the compositions of the present invention provide a potent therapeutic effect without or while reducing the adverse effects on normal, healthy cells. Furthermore, the combination of catechins and *Capsicum* extracts have a synergistic effect for the inhibition of cancer cell growth and in the inhibition of tNOX.

Significantly the effect of the catechins such as EGCg is reversible, i.e., if the EGCg is removed, cancer cells resume normal rates of growth. Other discoveries include EGCg is rapidly cleared from the blood and metabolized, cancer cells must be inhibited from growing for 48 to 72 hours before EGCg-induced apoptosis occurs, and when cancer cells are challenged with $10^{-7}$ M EGCg every two hours during the day, their growth is inhibited, but during the night normal cell growth resumes in the absence of further EGCg addition. Thus, one embodiment of the invention is directed to the administration of *Capsicum* extracts with catechins followed by administration of sustained release catechin formulations so that a constant level of the catechins is maintained.

The invention comprises formulations (e.g., specific combination of catechins and specific levels) of green tea polyphenols, in particular, catechins, for the prevention and/or treatment of cancer. The typical percentage of the individual catechins in green tea extracts is 10–15% EGCg, 2–3% ECG, 2% EC, and 2–3% EGC (Suganuma et al., 1999, Can. Res. 59:44–47).

In contrast, in one embodiment of the present invention, EGCg constitutes at least 30% of the total catechins. In a preferred embodiment, EGCg constitutes about 35% to about 45% of the total catechins. In a more preferred embodiment, EGCg constitutes about 40% of the total catechins.

Although the invention encompasses the use of a composition containing certain levels of EGCg alone, it is preferred that EGCg be used in combination with other catechins, more specifically, those described infra.

In another embodiment, EGCg constitutes at least 30% of the total catechins and ECG constitutes at least 5% of the total catechins. In a preferred embodiment, EGCg constitutes about 35% to about 45% of the total catechins and ECG constitutes about 10% to about 20% of the total catechins. In a more preferred embodiment, EGCg constitutes about 40% of the total catechins and ECG constitutes about 15% of the total catechins.

In another embodiment, EGCg constitutes at least 30% of the total catechins and EC constitutes at least 3% of the total catechins. In a preferred embodiment, EGCg constitutes about 35% to about 45% of the total catechins and EC constitutes about 3% to about 15% of the total catechins. In a more preferred embodiment, EGCg constitutes about 40% of the total catechins and EC constitutes about 7% of the total catechins.

In another embodiment, EGCg constitutes a negligible amount of the catechin formulation.

In an additional embodiment, EGCg constitutes at least 30% of the total catechins and EGC constitutes at least 1% of the total catechins. In a preferred embodiment, EGCg constitutes about 35% to about 45% of the total catechins and EGC constitutes about 2% to about 5% of the total catechins. In a more preferred embodiment, EGCg constitutes about 40% of the total catechins and EGC constitutes about 3% of the total catechins.

In an additional embodiment, EGCg constitutes at least 30% of the total catechins, EC constitutes at least 3% of the total catechins, and ECG constitutes at least 5% of the total catechins. In a preferred embodiment, EGCg constitutes about 35% to about 45% of the total catechins, EC constitutes about 3% to about 15% of the total catechins, and ECG constitutes about 10% to about 20% of the total catechins. In a more preferred embodiment, EGCg constitutes about 40% of the total catechins, EC constitutes about 7% of the total catechins, and ECG constitutes about 15% of the total catechins.

In yet another embodiment, EGCg constitutes at least 30% of the total catechins, EC constitutes at least 3% of the total catechins, and EGC constitutes at least 1% of the total catechins. In a preferred embodiment, EGCg constitutes about 35% to about 45% of the total catechins, EC constitutes about 3% to about 15% of the total catechins, and EGC constitutes about 2% to about 5% of the total catechins. In a more preferred embodiment, EGCg constitutes about 40% of the total catechins, EC constitutes about 7% of the total catechins, and EGC constitutes about 3% of the total catechins.

In yet another embodiment, EGCg constitutes at least 30% of the total catechins, EC constitutes at least 3% of the total catechins, ECG comprises at least 5% of the total catechins, and EGC constitutes at least 1% of the total catechins. In a preferred embodiment, EGCg constitutes about 35% to about 45% of the total catechins, EC constitutes about 5% to about 15% of the total catechins, ECG constitutes about 10% to about 20% of the total catechins, and EGC constitutes 2% to about 5% of the total catechins. In a more preferred embodiment, EGCg constitutes about 40% of the total catechins, EC constitutes about 7% of the total catechins. ECG constitutes about 15% of the total catechins, and EGC constitutes about 3% of the total catechins.

In yet another embodiment, EGCg constitutes at least 30% of the total catechins, EC constitutes at least 3% of the total catechins, ECG constitutes at least 5% of the total catechins, EGC constitutes at least 1% of the total catechins, and C constitutes at least 5% of the total catechins. In a preferred embodiment, EGCg constitutes about 35% to about 45% of the total catechins, EC constitutes about 5% to about 15% of the total catechins, ECG constitutes about 10% to about 20% of the total catechins, EGC comprises 2% to about 5% of the total catechins, and C comprises about 10% to about 20% of the total catechins. In a more preferred embodiment, EGCg constitutes about 40% of the total catechins, EC constitutes about 7% of the total catechins. ECG constitutes about 15% of the total catechins, EGC constitutes about 3% of the total catechins, and C constitutes about 15% of the total catechins.

The level of caffeine is generally less than about 5% and is preferably less than 0.5% of the polyphenols.

The invention encompasses all pharmaceutically acceptable derivatives of the catechins listed supra, and combinations thereof, in combination with *Capsicum* extract.

The invention comprises a mixture of catechins, including but not limited to the percentages of the polyphenols described supra, formulated as sustained release compositions. In a specific embodiment, the invention comprises a mixture of catechins which when administered to a human results in circulating levels of EGCg is maintained between $10^{-9}$ and $10^{-4}$ M for at least 12 hours in a 24 hour time period. In a preferred embodiment for the prevention of cancer, the circulating levels of all catechins in the catechin mixture is maintained up to $10^{-7}$ M. In a preferred embodiment for the treatment of cancer, the circulating levels of all catechins in the catechin mixture is maintained up to $10^{-7}$ M. The levels are either circulating in the patient systemically, or in a preferred embodiment, localized to the tumor, and in a most preferred embodiment, localized to the cell surface of the cancer cells.

It is understood that the catechin and active ingredient(s) of *Capsicum* extract levels are maintained over a certain period of time as is desired and can be easily determined by one of skill in the art using this disclosure and available pharmaceutical compendia.

Such sustained and/or timed release formulations may be made by sustained release means or delivery devices that are well known to those of ordinary skill in the art, such as those described in U.S. Pat. Nos.: 3,845,770, 3,916,899, 3,536,809, 3,598,123, 4,008,719, 4,710,384, 5,674,533, 5,059,595, 5,591,767, 5,120,548, 5,073,543, 5,639,476, 5,354,556, and 5,733,566, the disclosures of which are each incorporated herein by reference. These pharmaceutical compositions can be used to provide slow or sustained release of one or more of the active ingredients using, for example, hydropropylmethyl cellulose, other polymer matrices, gels, permeable membranes, osmotic systems, multilayer coatings, microparticles, liposomes, microspheres, or the like, or a combination thereof to provide the desired release profile in varying proportions. Suitable sustained release formulations known to those of ordinary skill in the art, including those described herein, may be readily selected for use with the pharmaceutical compositions of the invention. Thus, single unit dosage forms suitable for oral administration, such as, but not limited to, tablets, capsules, gelcaps, caplets, powders, and the like, that are adapted for sustained release are encompassed by the present invention.

In a highly preferred embodiment, the sustained release formulation contains active ingredients such as, but not limited to, microcrystalline cellulose, maltodextrine, ethylcellulose, and magnesium stearate. In yet another highly preferred embodiment, the formulation is synthesized with a CapsuDar® SR (Biodar, Yavne, Israel) microencapsulation which consists of the active ingredients microcrystalline cellulose, maltodextrine, ethylcellulose, and magnesium stearate.

As described above, all known methods for encapsulation which are compatible with the properties of tea catechins are compassed by this invention. The sustained release formulation is encapsulated by coating particles or granules of the pharmaceutical composition of the invention with varying thicknesses of slowly soluble polymers or by microencapsulation. In a preferred embodiment, the sustained release formulation is encapsulated with a coating material of varying thickness (e.g., about 1 micron to 200 microns) that allows the dissolution of the pharmaceutical composition about 48 hours to about 72 hours after administration to a mammal. In another embodiment, the coating material is a food approved additive. In yet another embodiment, the coating material is sold under the trademark Eudragit RS or RL (Rohm Pharma, Germany).

In another embodiment, the sustained release formulation is a matrix dissolution device, which is prepared by compressing the drug with a slowly soluble polymer carrier into a tablet. In one preferred embodiment, the coated particles have a size range between about 0.1 to about 300 microns, as disclosed in U.S. Pat. Nos. 4,710,384 and 5,354,556, which are incorporated herein by reference in their entireties. Each of the particles is in the form of a micromatrix, with the active ingredient uniformly distributed throughout the polymer.

Sustained release formulations such as those described in U.S. Pat. No. 4,710,384, which is incorporated herein by reference in its entirety, have a relatively high percentage of plasticizer in the coating in order to permit sufficient flexibility to prevent substantial breakage during compression. The specific amount of plasticizer varies depending on the nature of the coating and the particular plasticizer used. The amount may be readily determined empirically by testing the release characteristics of the tablets formed. If the medicament is being released too quickly, then more plasticizer is used. Release characteristics are also a function of the thickness of the coating. When substantial amounts of plasticizer are used, the sustained released capacity of the coating diminishes. Thus, the thickness of the coating may be increased slightly to make up for an increase in the amount of plasticizer. Generally, the plasticizer in such an embodiment will be present in an amount of about 15 to 30 percent of the sustained release material in the coating, preferably 20 to 25 percent and the amount of coating will be from 10 to 25 percent of the weight of active material, preferably 15 to 20 percent. Any conventional pharmaceutically acceptable plasticizer may be incorporated into the coating.

The disclosure of U.S. Pat. No. 6,410,052, which is directed to the use of sustained release formulations of catechins for the treatment and prevention of cancer, is hereby incorporated by reference in its entirety.

In one embodiment, the *Capsicum* extracts comprises an extract isolated from a naturally-occurring source. In a preferred embodiment, the *Capsicum* extract comprises a amidase-treated *Capsicum* extract. Generally, the ratio of *Capsicum* extract to tea catechins is 1:1 to 1:500, preferably 1:1:100, desirably 1:25.

The treatment of the water extract of *Capsicum* can be accomplished by bacterial or fungal enzymes, such as amidases. An example of such an amidase is an amidase isolated from *Pseudomonas aeruginosa*, which is available from Sigma Chemical Co. (St. Louis, Mo.) and disclosed by Brown et al., which is incorporated by reference in its entirety (Brown et al., 1969, J. Gen. Microbiol. 1969 57(2): 273–85). Without wishing to be bound by theory, at least benefit of amidase treatment of a hot pepper extract is that the capsaicin content is reduced, and as a result, the sensation of heat from that extract is decreased, thereby reducing discomfort of the consumer.

The extraction of the active ingredients of this invention from *Capsicum* may be accomplished by the following process. The dried *Capsicum* peppers are finely ground and reconstituted in water. The mixture is incubated with a bacterial or fungal extract rich in amidases, such as a *Pseudomonas aeruginosa* extract, which enzyme acts to reduce the apparent "hot sensation" where the extract is from a so-called hot pepper. Alternatively, the amidases may be purified, such as an amidase isolated from *Pseudomonas aeruginosa*, which is available from Sigma Chemical Co. (St. Louis, Mo.). The mixture is incubated for several days, and then neutralized by heating or adding alcohol. It is understood that one or ordinary skill in the art may vary the incubation time based on one's needs and would take into account the specific enzymatic activity of the particular amidase used in the reaction, such as, for example, one of skill may be the activity and instructions available from the manufacture if the amidase is purchased as above. Denatured proteins are removed by centrifugation or filtration 0.22 μm or 0.45 μm filters are preferred. The supernatant contains the active ingredients of *Capsicum* of the present invention.

Cancers that can be treated by the methods and with the compositions of the present invention include, but not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

In a preferred embodiment, the cancer is one where circulating levels of tNOX are present in the sera of patients suffering from said cancer, e.g., rectal carcinoma, colon carcinoma, breast carcinoma, ovarian carcinoma, small cell lung carcinoma, colon carcinoma, chronic lymphocytic carcinoma, hairy cell leukemia, osophogeal carcinoma, prostate carcinoma, breast cancer, myeloma, and lymphoma, see e.g., U.S. Pat. No. 5,605,810, which is incorporated by reference in its entirety.

In a preferred embodiment, the patient already has cancer and is undergoing treatment for said cancer. In a specific embodiment, the patient already has cancer but no metastasis (secondary cancer). In another specific embodiment, the patient already has cancer plus a metastatic cancer. In another specific embodiment, the patient having a cancer is immunosuppressed by reason of having undergone anticancer therapy (e.g., chemotherapy or radiation) prior to administration of the catechin/*Capsicum* extract complexes of the invention.

In another specific embodiment, the cancer is a tumor. In a preferred embodiment, the tumor is a tumor of epithelial tissue, lymphoid tissue, connective tissue, bone, or central nervous system.

The invention encompasses administration of a composition comprising both the catechin formulations and *Capsicum* extract formulations described herein.

In one embodiment, a sustained release catachin formulation, as described in herein and in U.S. Pat. No. 6,410,052, which is hereby incorporated by reference in its entirety, is used in combination with a *Capsicum* extract formulation described herein. In a preferred embodiment, a sustained release catechin formulation is used in combination with a *Capsicum* extract.

The invention encompasses the catechin formulations and *Capsicum* extract formulations as described herein administered in combination with other therapeutic agents, such as anti-cancer drugs. The therapeutic agents include, but are not limited to adriamycin and adriamycin conjugates, mechlorethamine, cyclophosphamide, ifosfamide, melphalan, chlorambucil, hexamethylmelamine, thiotepa, busulfan, carmustine, lomustine, semustine, streptozocin, dacarbazine, methotrexate, fluorouacil, floxuridie, cytarabine, mercaptopurine, thioguanine, pentostatin, vinblastine, vincristine, etoposide, teniposide, actinomycin D, daunorubicin, doxorubicin, bleomycin, plicamycin, mitomycin, L-asparaginase, interferon-alpha, cisplatin, carboplatin, mitoxantrone, hydroxyurea, procarbazine, mitotane, aminoglutethimide, prednisone, hydroxyprogesterone caproate, medroxyprogesterone acetate, megestrol acetate, diethylstilbestrol, ethinyl estradiol, tamoxifen, testosterone propionate, fluoxymesterone, flutamide, leuprolide, acetogenins, e.g., bullatacin, and quassanoids, e.g. simalikalactone D and glaucarubolone, and pharmaceutically acceptable derivatives thereof. The therapeutic agents which inhibit tNOX and cancer cell growth include adriamycin, bullatacin, simalikalactone D, and glaucarubolone has been demonstrated in U.S. Pat. No. 5,605,810, which is incorporated by reference in its entirety.

The invention also embodies the catechin formulations, *Capsicum* extracts formulations, anti-cancer agents, and combinations thereof for the treatment of cancer patients undergoing chemotherapy and/or irradiation for a primary cancer. In a preferred embodiment, the catechin formulations, anti-cancer agents, and combinations thereof provides a method for treating the metastasized, i.e. secondary cancer, in said patients.

In another embodiment, the secondary agent administered, in addition to the catechin formulations, includes a monoclonal antibody directed against tNOX for combination therapy. A monoclonal antibody to the human tNOX protein isolated from the sera of cancer patients has already successfully been used in the expression cloning of tNOX from HeLa cells (Chueh et al., 1997, Arch. Biochem. Biophys. 342:38–44).

Compositions of the invention which comprise catechin and *Capsicum* extract may be formulated into pharmaceutical preparations for administration to mammals for treatment of cancer. In a preferred embodiment, the mammal is a human.

Compositions comprising catechin(s) and *Capsicum* extract formulated in a compatible pharmaceutical carrier may be prepared, packaged, and labeled for treatment of carcinoma, glioma, astrocytoma, medulloblastoma, craniopharyngioma, ependymoma, pinealoma, the indicated cancer, such as human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

The compositions of the invention can be formulated as sustained and/or timed release formulations. The levels of circulating catechin compositions must be maintained above some minimum therapeutic dose to reduce the number of cancer cells and/or prevent cancer. In one embodiment, the reduction in the number of cancer cells is a result of cell death or apoptosis. In another embodiment, the reduction in the number of cancer cells is a result of inhibition of cell growth. In yet another embodiment, the reduction in the number of cancer cells is a result of cell growth arrest.

All sustained release pharmaceutical products have a common goal of improving drug therapy over that achieved by their non-sustained counterparts. Ideally, the use of an optimally designed sustained release preparation in medical treatment is characterized by a minimum of drug substance being employed to cure or control the condition. Advantages of sustained release formulations may include extended activity of the composition; reduced dosage frequency; and increased patient compliance. In addition, sustained release formulations can be used to affect the time of onset of action or other characteristics, such as blood levels of the composition, and thus can affect the occurrence of side effects.

The sustained release formulations of the invention are designed to initially release an amount of the therapeutic composition that promptly produces the desired therapeutic effect, and gradually and continually release of other amounts of compositions to maintain this level of therapeutic effect over an extended period of time. In order to maintain this constant level in the body, the therapeutic composition must be released from the dosage form at a rate that will replace the composition being metabolized and excreted from the body.

The sustained release of an active ingredient may be stimulated by various inducers, for example pH, temperature, enzymes, water, or other physiological conditions or compounds. The term "sustained release component" in the context of the present invention is defined herein as a compound or compounds, including, but not limited to, polymers, polymer matrices, gels, permeable membranes, liposomes, microspheres, or the like, or a combination thereof, that facilitates the sustained release of the active ingredient.

If the complex is water-soluble, then it may be formulated in an appropriate buffer, for example, phosphate buffered saline or other physiologically compatible solutions. Alternatively, if the resulting complex has poor solubility in aqueous solvents, then it may be formulated with a non-ionic surfactant such as Tween, or polyethylene glycol. Thus, the compounds and their physiologically acceptable solvates may be formulated for administration by inhalation or insufflation (either through the mouth or the nose) or oral, buccal, parenteral, rectal administration or, in the case of tumors, directly injected into a solid tumor.

For oral administration, the pharmaceutical preparation may be in liquid form, (e.g., solutions, syrups or suspensions), or may be presented as a drug product (e.g., capsule or powder) for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art. In a preferred embodiment, the pharmaceutical composition may take the form of a capsule or powder to be dissolved in a liquid for oral consumption.

Preparations for oral administration may be suitably formulated to give controlled release of the active compound. In a preferred embodiment, the compounds of the present invention are formulated as controlled release powders of discrete micro-particles which can be readily formulated in liquid form. The sustained release powder comprises particles containing an active ingredient and optionally, an excipient with at least one non-toxic polymer.

The powder can be dispersed or suspended in a liquid vehicle and will maintain its sustained release characteristics for a useful period of time. These dispersions or suspensions have both chemical stability and stability in terms of dissolution rate. The powder may contain an excipient comprising a polymer, which may be soluble, insoluble, permeable, impermeable, or biodegradable. The polymers may be polymers or copolymers. The polymer may be a natural or synthetic polymer. Natural polymers include polypeptides (e.g., zein), polysaccharides (e.g., cellulose), and alginic acid. Representative synthetic polymers include those described, but not limited to, those described in column 3, lines 33–45 of U.S. Pat. No. 5,354,556 which is incorporated by reference in its entirety. Particularly suitable polymers include those described, but not limited to, those described in column 3, line 46-column 4, line 8 of U.S. Pat. No. 5,354,556 which is incorporated by reference in its entirety.

For buccal administration, the compositions may take the form of tablets or lozenges formulated in conventional manner.

The sustained release compounds of the invention may be formulated for parenteral administration, e.g., by intramuscular injections or implants for subcutaneous tissues and various body cavities and transdermal devices.

Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

In a preferred embodiment, intramuscular injections are formulated as aqueous or oil suspensions. In an aqueous suspension, the sustained release effect is due to, in part, a reduction in solubility of the active compound upon complexation or a decrease in dissolution rate. A similar approach is taken with oil solutions and suspensions, wherein the release rate of an active compound is determined by partitioning of the active compound out of the oil into the surrounding aqueous medium. Only active compounds which are oil soluble and have the desired partition characteristics are suitable. Oils that may be used for intramuscular injection include, but are not limited to, sesame, olive, arachnis, maize, almond, cottonseed, and castor oil.

A highly developed form of drug delivery that imparts sustained release over periods of time ranging from days to years is to implant a drug-bearing polymeric device subcutaneously or in various body cavities. The polymer material used in an implant, which must be biocompatible and nontoxic, include but are not limited to hydrogels, silicones, polyethylenes, ethylene-vinyl acetate copolymers, or biodegradable polymers.

The compounds may also be formulated in rectal compositions such as suppositories or retention enemas, e.g., containing conventional suppository bases such as cocoa butter or other glycerides.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The invention also provides kits for carrying out the therapeutic regimens of the invention. Such kits comprise in one or more containers having therapeutically or prophylactically effective amounts of the catechin/*Capsicum* extract complexes in pharmaceutically acceptable form. The catechin/*Capsicum* extract complex in a vial of a kit of the invention may be in the form of a pharmaceutically acceptable solution, e.g., in combination with sterile saline, dextrose solution, or buffered solution, or other pharmaceutically acceptable sterile fluid. Alternatively, the complex may be lyophilized or desiccated; in this instance, the kit optionally further comprises in a container a pharmaceutically acceptable solution (e.g., saline, dextrose solution, etc.), preferably sterile, to reconstitute the complex to form a solution for injection purposes.

In another embodiment, a kit of the invention further comprises a needle or syringe, preferably packaged in sterile form, for injecting the complex, and/or a packaged alcohol pad. Instructions are optionally included for administration of catechin complexes by a clinician or by the patient.

In one embodiment of this invention, a formulation comprising catechins and *Capsicum* extracts may be used as a dietary or nutritional supplement for the prevention of cancer. In this embodiment, the total daily dose ranges of the active catechins for the conditions described herein are generally from about 10 mg to about 800 mg administered in divided doses administered parenterally or orally. A preferred total daily dose is from about 50 mg to about 400 mg of the active catechins and *Capsicum* extracts.

In a another embodiment, a total daily dose of a formulation may be used as a dietary supplement is about 10 mg to about 800 mg of active catechins and *Capsicum* extracts administered twice daily (e.g., in the morning and the evening) at a dose of about 5 mg to about 400 mg. The dosage forms and compositions may comprise any of the forms and compositions described supra. In a preferred embodiment, the sustained release formulation comprising catechins is a tablet, capsule, gel, or a liquid-soluble powder which is administered in combination with a *Capsicum* extract.

In another embodiment of the invention, the magnitude of a therapeutic dose of catechins and *Capsicum* extracts in the acute or chronic management of cancer varies with the severity of the condition to be treated and the route of administration. The dose and dose frequency also vary according to the age, body weight, condition and response of the individual patient, and the particular catechin and *Capsicum* extract combination used. All combinations described herein are encompassed as therapeutic, active catechin and *Capsicum* extract mixtures and it is understood that one of skill in the art would be able to determine a proper dosage of particular catechin and *Capsicum* extract mixtures using the parameters provided in the invention. In general, the total daily dose ranges of the active catechins and *Capsicum* extracts for the conditions described herein are generally from about 10 mg to about 2000 mg of catechins and about 1 mg to about 1000 mg of *Capsicum* extract administered in divided doses administered parenterally or orally or topically. A preferred total daily dose is from about 200 mg to about 600 mg of the active catechins and *Capsicum* extracts.

At least one dosage form must be a sustained release formulation of tea catechins. Preferably, the sustained release formulation is provided in a manner that maintains a constant level of catechins for at least 12 hours of a 24 hour period. The *Capsicum* extract may be administered to the patient in either a single formulation which contains both the tea catechins and *Capsicum* extract or, alternatively, the *Capsicum* extract may be separately administered. In a highly preferred embodiment, this regimen of maintaining the constant level of catechins is maintained for at least three days (72 hours).

For example, in one embodiment, the daily dose ranges of catechins and *Capsicum* extracts for the conditions described herein are generally from about 10 to about 100 mg per kg weight for catechins and about 0.1 to about 100 mg/kg of *Capsicum* extract. Preferably the catechin formulation of the invention is given daily until remission, followed by two to ten additional cycles, each lasting about 60 days in duration. When the dose is administered orally, a sustained release formulation is preferred so that a fairly constant level of catechins is provided over the course of treatment, which is generally at least 48 hours and preferably at least 96 hours per cycle. As the catechin and *Capsicum* extract are not particularly toxic, the formulation may be administered for as long as necessary to achieve the desired therapeutic effect.

In the case where an intravenous injection or infusion composition is employed, a suitable dosage range for use is generally about one-tenth of that described in the preceding paragraph.

For treatment of solid tumors, a preferred dosing regimen involves intravenous infusion of about 1 to about 10 mg per kg body weight of catechins and about 0.1 to about 100 mg/kg of *Capsicum* extract. This daily treatment protocol is repeated until the tumor growth tumor is inhibited or when the tumor shows signs of regression.

In an alternative embodiment of the invention, the effect of the therapy with catechins and *Capsicum* extracts on cancer treatment can be monitored by any methods known in the art, including but not limited to monitoring circulating tNOX activity in patient sera, as well as more traditional approaches such as determining levels of tumor specific antigens and putative biomarkers, e.g., carcinoembryonic antigens (CEA), alpha-fetoprotein; and changes in morphology and/or size using computed tomographic scan and/or sonogram.

Desirable blood levels may be maintained by a continuous infusion of catechins and *Capsicum* extracts as ascertained by plasma levels. It should be noted that the attending physician would also know how to and when to adjust treatment to higher levels if the clinical response is not adequate (precluding toxic side effects, if any).

Again, any suitable route of administration may be employed for providing the patient with an effective dosage of the catechin and *Capsicum* extract combination of this invention. Dosage forms include tablets, troches, cachet, dispersions, suspensions, solutions, capsules, gel caps, caplets, compressed tablets, sustained release devices, patches, and the like.

The pharmaceutical compositions of the present invention comprise catechins as the active ingredients, as well as pharmaceutically acceptable salts thereof, and may also contain a pharmaceutically acceptable carrier, and optionally, other therapeutic ingredients. The term "pharmaceutically acceptable salts" refers to salts prepared from pharmaceutically acceptable non-toxic acids and bases, including inorganic and organic acids and bases.

The pharmaceutical compositions include compositions suitable for oral and parenteral (including subcutaneous, intramuscular, intrathecal, intravenous, and other injectables) routes, although the most suitable route in any given case will depend on the nature and severity of the condition being treated.

In addition, the catechin and *Capsicum* extract carrier could be delivered via charged and uncharged matrices used as drug delivery devices such as cellulose acetate membranes, also through targeted delivery systems such as fusogenic liposomes attached to antibodies or specific antigens.

In practical use, catechins and *Capsicum* extracts can be combined as the active ingredient(s) in intimate admixture with a pharmaceutical carrier according to conventional pharmaceutical compounding techniques. The carrier may take a wide variety of forms depending on the form of preparation desired for administration, e.g., oral or parenteral (including tablets, capsules, powders, intravenous injections or infusions). In preparing the compositions for oral dosage form any of the usual pharmaceutical media may be employed, e.g., water, glycols, oils, alcohols, flavoring agents, preservatives, coloring agents, and the like; in the case of oral liquid preparations, e.g., suspensions, solutions, elixirs, liposomes and aerosols; starches, sugars, microcrystalline cellulose, diluents, granulating agents, lubricants, binders, disintegrating agents, and the like in the case of oral solid preparations e.g., powders, capsules, and tablets. In preparing the compositions for parenteral dosage form, such as intravenous injection or infusion, similar pharmaceutical media may be employed, e.g., water, glycols, oils, buffers, sugar, preservatives and the like know to those skilled in the art. Examples of such parenteral compositions include, but are not limited to Dextrose 5% (w/v), normal saline or other solutions. The total dose of the catechins and *Capsicum* extracts extract may be administered in a vial for intravenous injection, e.g., ranging from about 0.01 to about 1000 mg per kg body weight of catechins and *Capsicum* extract. The volume of dilution fluid varies according to the total dose administered and over the length of the period of time of administration.

In another embodiment, the invention encompasses the daily dose ranges of catechins and *Capsicum* extract for the conditions described herein are generally from about 0.1 to about 15 mg per kg body weight administered in divided doses administered orally. Preferably the catechin formulation of the invention is given daily, or until remission, followed by two to ten additional cycles, each lasting about 60 days in duration. When the dose is administered orally, a sustained release formulation is preferred so that a fairly constant level of catechins is provided over the course of treatment, which is generally at least 48 hours and preferably at least 96 hours per cycle. As the catechin and *Capsicum* extracts extracts are not particularly toxic, the formulation may be administered for as long as necessary to achieve the desired therapeutic effect. In the case where an intravenous injection or infusion composition is employed, a suitable dosage range for use is, e.g., from about 0.01 to about 1.5 mg per kg body weight of catechins and *Capsicum* extract total daily.

For treatment of solid tumors, a preferred dosing regimen involves intravenous infusion of the active catechins and *Capsicum* extracts of the invention, as described above, in the amount of about 0.01 to about 10 mg per kg body weight per day. This daily treatment protocol is repeated once per month until the tumor growth tumor is inhibited or when the tumor shows signs of regression.

The effect of the therapy with catechins and *Capsicum* extracts on cancer treatment can be monitored by methods stated supra. Similarly, pharmaceutical compositions and routes of administration are similar as those described supra.

For the purposes described above, the invention also encompasses methods for monitoring patient response to tea catechins and *Capsicum* extracts. By monitoring circulating tNOX activity in patient sera, it will be possible to determine therapeutic dosages and to monitor therapeutic benefit from tea catechins and *Capsicum* extracts. The response of neoplastic cells to the subject compositions may be monitored by assaying the blood or urine of the patient for the NOX activity that is responsive to the catechin and *Capsicum* extract compositions, i.e., tNOX. Various assays may be used to monitor activity, such as a NOX assay for neoplasia determination see e.g., U.S. Pat. No. 5,605,810. By following the above monitoring procedures, an effective dosage of the subject compositions may be administered in accordance with the requirement of an individual patient.

EXAMPLE

Synergistic Effect of Catechins and *Capsicum* Extracts

HeLa (ATCC CCL2) cells were grown in 150 cm' flasks in Minimal Essential Medium (Gibco), pH 7.4, at 37° C. with 10% bovine calf serum (heat inactivated, plus 50 mg/l gentamicin sulfate (Sigma). A mouse mammary tumor subpopulation line 4T1 arising from a BALB/cfC3H mouse (Miller et al., 1981, Brit. J. Cancer 56:561 and Miller et al., 1990, Invasion Metastasis 10:101) was grown in DME 10, Dulbecco's modified Eagle's medium supplemented with 5% fetal calf serum, 5% newborn calf serum, 1 mM mixed non-essential amino acids, 2 mM L-glutamine, penicillin (100 units/ml), and streptomycin (100 µg/ml).

Cells were quantitated using a standard cytotoxicity assay (Matthews, N. and Neale, M. L. In Lymphokines and Interferons. A Practical Approach. Clemens, M. J. et al., eds. IRL Press, Oxford, p. 221 (1987)).

NADH oxidase activity may be monitored and measured by virtue of the decrease in absorbance at 340 µm wavelength. A millimolar extinction coefficient of 6.22 for NADH was used to calculate rates of NADH oxidation. Additional tests are such as those described by Morre, 1994, Bioenerg. Biomemb. 26:421, and Chueh et al., 1997, J. Biol. Chem. 272:11221, which are incorporated by reference in their entireties.

Figure 1A:
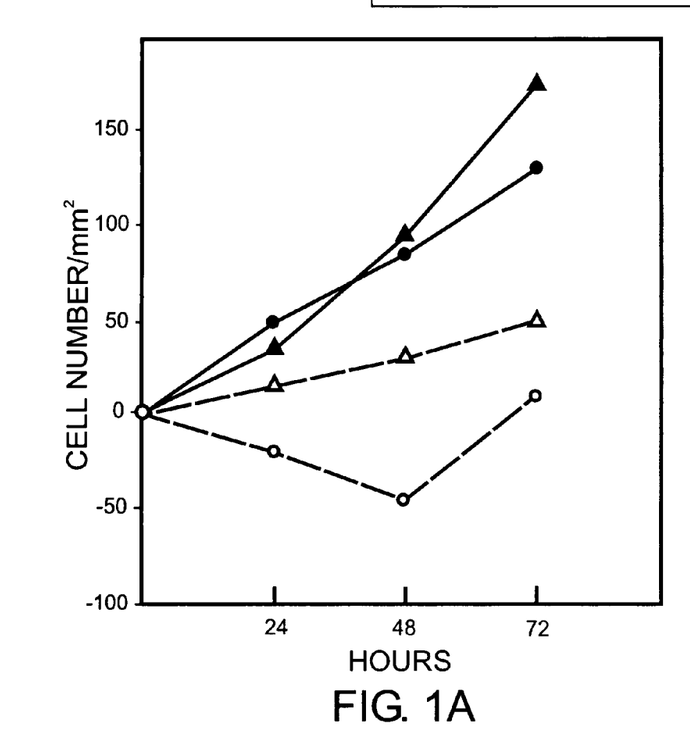
FIG. 1A–1D shows the effects of combinations of three times daily additions of tea catechins (Tegreen™) or a mixture of an amidase-treated *Capsicum* extract plus green tea extract (Capsibiol-T®), final concentration $10^{-8}$ M, in combination with Tegreen™ or time-release tea catechins (Tegreen) overnight.
Figure 1B:
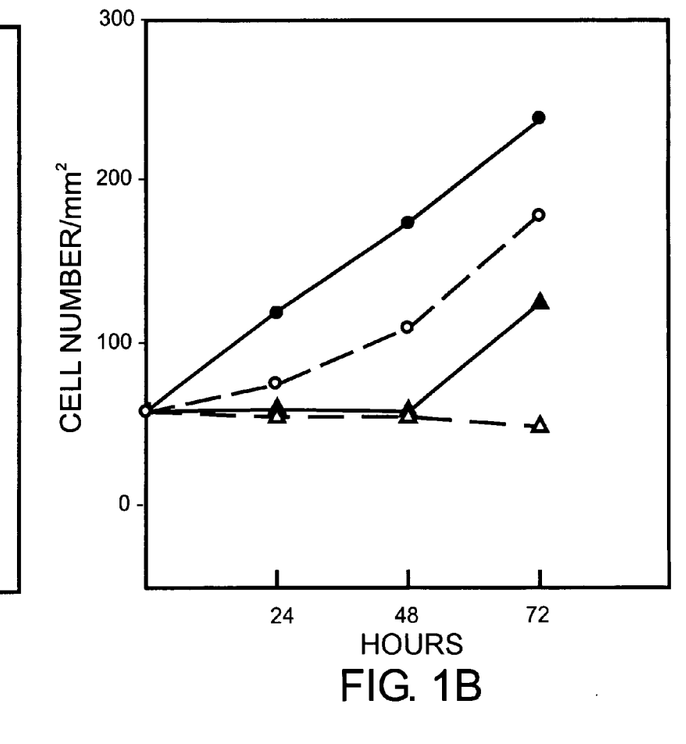
Figure 1C:
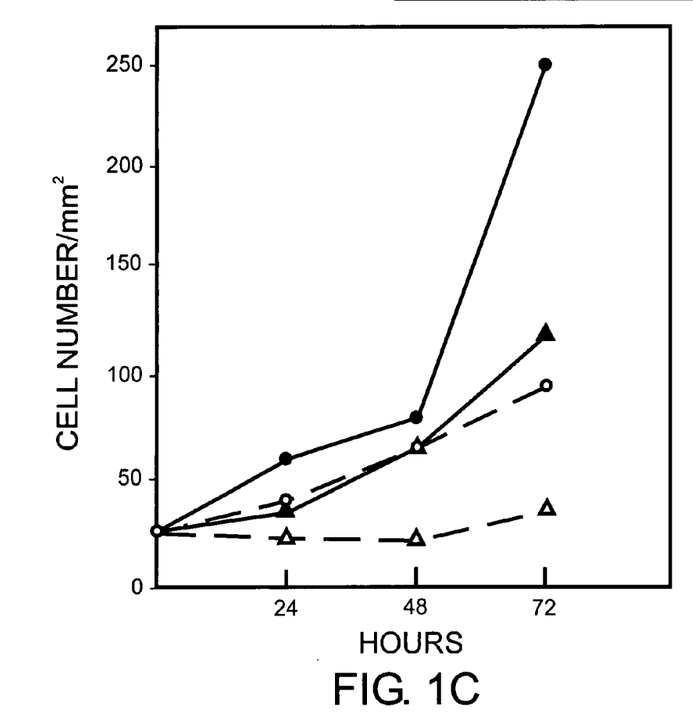
Figure 1D:
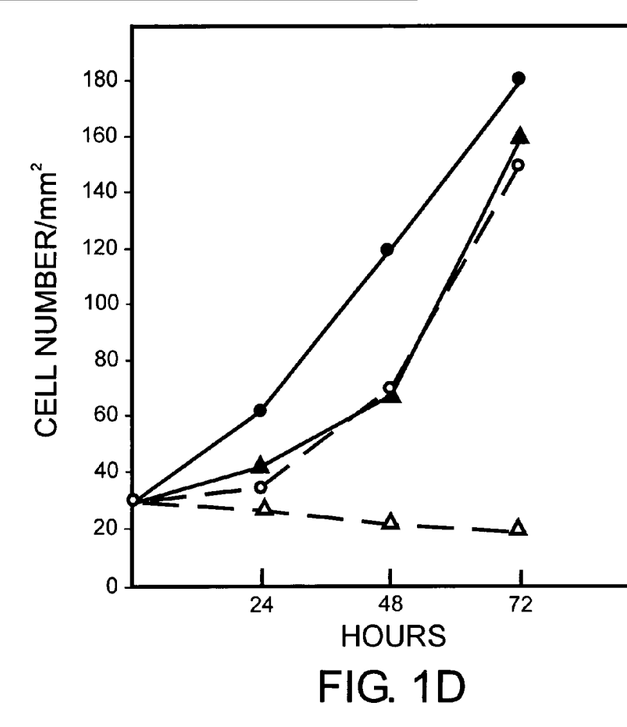

The effect of a sustained release formulation of a commercially supplied tea catechin concentrate (Tegreen™, Pharmanex, Brisbane, Calif.) in combination with a *Capsicum* extract on the inhibition of cancer cell growth was determined and the results are presented in FIG. 1. To model the efficacy of the time release Tegreen™, HeLa cells in culture were treated three times daily (9:00 am, noon, and 3:00 pm) with either 10–5 M Tegreen™ (10–8 on final concentration) or a mixture of amidase-treated *Capsicum* extracts plus a lyophilized extract of green tea (Capsibiol-T) followed by Tegreen™ or P3389 sustained release Tegreen™ at 5:00 pm. With either Tegreen™ three times daily and Tegreen™ overnight (FIG. 1A) or Capsibiol-T® three times daily and Tegreen™ overnight (FIG. 6C), the HeLa cells were inhibited but not recovered and continued to grow. However, with either Tegreen™ three times daily followed by 10–5 M P-3389 (ca. 10.8 M final concentration when released) or with Capsibiol-T three times daily followed by P-3389 overnight, not only was cell growth inhibited, but the inhibited cells failed to recover over 72 hours and were killed.

These studies demonstrate that both the long term efficacy of the sustained-release tea catechin composition (18 hours) in the nanomolar concentration range and the inability of non-sustained release preparations to effectively reduce apoptosis at these same nanomolar concentrations. A serum or (tumor) level of 10 to 100 mM EGCg might be considered as a useful target level to maintain or to not drop below nighttime use of a sustained-release tea catechin preparation.

All references cited herein are hereby incorporated by reference in their entireties to the extent not inconsistent with the present disclosure.

The present invention is not to be limited in scope by the specific disclosure provided herein to illustrate certain embodiments of the invention. Indeed, various modifications of the invention in addition to those described will become apparent to those skilled in the art from the foregoing description and accompanying figures. Such modifications are intended to fall within the scope of the appended claims.

We claim:

1. A method for treating cancer in a mammal which comprises administering to a mammal in need of cancer treatment, wherein the cancer is a type having cancer cells which express tNOX, a therapeutically effective amount of tea catechins and an amidase-treated *Capsicum* extract.

2. The method of claim 1, wherein the mammal is a human.

3. The method of claim 2 wherein the cancer is selected from a group comprising rectal carcinoma, colon carcinoma, breast carcinoma, ovarian carcinoma, small cell lung carcinoma, colon carcinoma, chronic lymphocytic carcinoma, hairy cell leukemia, esophogeal carcinoma, prostate carcinoma, breast cancer, myeloma, and lymphoma.

4. The method of claim 2 wherein the cancer is a tumor of epithelial tissue, lymphoid tissue, connective tissue, bone, or central nervous system.

5. The method of claim 2 wherein the human is immunosuppressed by reason of having undergone anti-cancer therapy prior to administration of the catechins and *Capsicum* extract.

6. A method for reducing the incidence of or delaying the onset of cancer in a mammal which comprises administering to a mammal effective amounts of tea catechins and an amidase-treated aqueous extract of dried *Capsicum* fruits.

7. The method of claim 6 wherein said tea catechins and *capsicum* extract are administered at a frequency necessary to maintain said constant levels in serum of said mammal.

8. The method of claim 7 wherein said tea catechins are in a composition which comprises a sustained release formulation of tea catechins comprising tea catechins and at least one component which controls release of said catechins.

9. A method for treating cancer in a mammal which comprises administering to a mammal in need of therapy a therapeutically effective amount of a composition comprising one or more tea catechins, or pharmaceutically acceptable salts thereof, an amidase-treated aqueous extract of dried *Capsicum* fruits, in combination with an effective amount of at least one other chemotherapeutic agent.

10. The method of claim 9 in which said other anti-cancer agent is selected from a group consisting of adriamycin and adriamycin conjugates, mechlorethamine, cyclophosphamide, ifosfamide, melphalan, chlorambucil, hexamethylmelamine, thiotepa, busulfan, carmustine, lomustine, semustine, streptozocin, dacarbazine, methotrexate, fluorouracil, floxuridie, cytarabine, mercaptopurine, thioguanine, pentostatin, vinblastine, vincristine, etoposide, teniposide, actinomycin D, daunorubicin, doxorubicin, bleomycin, plicamycin, mitomycin, L-asparaginase, interferon-alpha, cisplatin, carboplatin, mitoxantrone, hydroxyurea, procarbazine, mitotane, aminoglutethimide, prednisone, hydroxyprogesterone caproate, medroxyprogesterone acetate, megestrol acetate, diethylstilbestrol, ethinyl estradiol, tamoxifen, testosterone propionate, fluoxymesterone, flutamide, leuprolide, acetogenins, e.g., bullatacin, and quassanoids, e.g. simalikalactone D and glaucarubolone, and pharmaceutically acceptable derivatives thereof.

11. The method of claim 1, 6 or 9 in which said administering is made parenterally, orally, or directly into the tumor.

12. The method of claim 1, 6 or 9 in which said administering is made via an implantation device.

13. The method of claim 1, 6 or 9 in which said administering is made with a sustained release formulation.

14. A composition for treating cancer in a mammal which comprises therapeutically effective amounts of tea catechins in combination with an amidase-treated *Capsicum* extract.

15. The composition of claim 14 wherein said tea catechins are formulated as a sustained release formulation.

16. The composition of claim 14 wherein the composition is formulated as an oral preparation comprising tablets or powders.

17. The composition of claim 14 wherein the composition is formulated as a sterile preparation.

18. The composition of claim 17 wherein the composition is formulated as a parenteral solution.

* * * * *